US008691516B2

(12) United States Patent
Lee et al.

(10) Patent No.: US 8,691,516 B2
(45) Date of Patent: Apr. 8, 2014

(54) MUTANT MICROORGANISM PRODUCING SUCCINIC ACID SIMULTANEOUSLY USING SUCROSE AND GLYCEROL, AND METHOD FOR PREPARING SUCCINIC ACID USING SAME

(75) Inventors: Sang Yup Lee, Daejeon (KR); Jeong Wook Lee, Gyeongsangnam-do (KR); Sol Choi, Jeju-do (KR); Jongho Yi, Busan (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 13/819,339

(22) PCT Filed: Aug. 30, 2011

(86) PCT No.: PCT/KR2011/006382
§ 371 (c)(1),
(2), (4) Date: Apr. 9, 2013

(87) PCT Pub. No.: WO2012/030130
PCT Pub. Date: Mar. 8, 2012

(65) Prior Publication Data
US 2013/0217087 A1    Aug. 22, 2013

(30) Foreign Application Priority Data
Aug. 30, 2010 (KR) .................. 10-2010-0084327

(51) Int. Cl.
*G01N 33/53* (2006.01)
*C12N 1/20* (2006.01)

(52) U.S. Cl.
USPC ............... 435/7.6; 435/252.35; 435/252.5

(58) Field of Classification Search
USPC ........... 435/252.3, 121, 252.5, 252.35, 7.6
See application file for complete search history.

(56) References Cited

U.S. PATENT DOCUMENTS 6,159,738 A    12/2000  Donnelly et al.
2011/0008851 A1*  1/2011  Scholten et al. ............ 435/121

FOREIGN PATENT DOCUMENTS

KR  10-2010-0070327 A   6/2010
WO      2009024294 A1   2/2009

OTHER PUBLICATIONS

Andersson, C., et al., "Effect of Different Carbon Sources on the Production of Succinic Acid Using Metabolically Engineered *Escherichia coli*", "Biotechnol. Prog.", Jan. 25, 2007, pp. 381-388, vol. 23.

Deutscher, J., et al., "How Phosphotransferase System-Related Protein Phosphorylation Regulates Carbohydrate Metabolism in Bacteria", "Microbiol. Mol. Biol. Rev.", Dec. 2006, pp. 939-1031, vol. 70, No. 4.
Goerke, B., et al., "Carbon catabolite repression in bacteria: many ways to make the most out of nutrients", "Nature Reviews", Aug. 2008, pp. 613-624, vol. 6.
Jantama, K., et al., "Combining Metabolic Engineering and Metabolic Evolution to Develop Nonrecombinant Strains of *Escherichia coli* C That Produce Succinate and Malate", "Biotechnology and Bioengineering", Oct. 30, 2007, pp. 1140-1153, vol. 99, No. 5.
Kuhnert, P., et al., "*Basfia succiniciproducens* gen. nov., sp. nov., a new member of the family Pasteurellaceae isolated from bovine rumen", "International Journal of Systematic and Evolutionary Microbiology", Jul. 31, 2009, pp. 44-50, vol. 60.
Lee, S., et al., "Genome-Based Metabolic Engineering of *Mannheimia succiniciproducens* for Succinic Acid Production", "Appl. Environ. Microbiol.", Mar. 2006, pp. 1939-1948, vol. 72, No. 3.
McKinlay, J., et al., "Prospects for a bio-based succinate industry", "Appl. Microbiol. Biotechnol.", Jul. 4, 2007, pp. 727-740, vol. 76.
Miller-Klein Associates, "Use of Tallow in Biodiesel", Oct. 2006, pp. 1-3.
Pettigrew, D., et al., "A Single Amino Acid Change in *Escherichia coli* Glycerol Kinase Abolishes Glucose Control of Glycerol Utilization In Vivo", "J. Bacteriol.", May 1996, pp. 2846-2852, vol. 178, No. 10.
Scholten, E., et al., "Succinic acid production by a newly isolated bacterium", "Biotechnol Lett", Jul. 24, 2008, pp. 2143-2146, vol. 30.
Song, H., et al., "Production of succinic acid by bacterial fermentation", "Enzyme and Microbial Technology", Jul. 2006, pp. 352-361, vol. 39.
Yazdani, S., et al., "Anaerobic fermentation of glycerol: a path to economic viability for the biofuels industry", "Current Opinion in Biotechnology", May 25, 2007, pp. 213-219, vol. 18.
Zeikus, J., et al., "Biotechnology of succinic acid production and markets for derived industrial products", "Appl. Microbiol. Biotechnol.", May 1999, pp. 545-552, vol. 51, No. 5.

(Continued)

*Primary Examiner* — Maryam Monshipouri
(74) *Attorney, Agent, or Firm* — Hultquist PLLC; Steven J. Hultquist; Mary B. Grant

(57) ABSTRACT

The present invention relates to a succinic acid-producing mutant microorganism that is able to utilize sucrose and glycerol simultaneously as carbon sources. More particularly, the present invention relates to a succinic acid-producing mutant microorganism that is able to utilize sucrose and glycerol simultaneously for succinic acid production, the mutant organism being obtained by relieving the mechanism of sucrose-mediated catabolite repression of glycerol in a succinic acid-producing microorganism. As described above, when the succinic acid-producing mutant microorganism is cultured, it utilizes sucrose and glycerol simultaneously so that succinic acid can be produced with high productivity in a maximum yield approaching the theoretical yield while the production of byproducts is minimized. In addition, according to the present invention, various reduced chemicals which have been produced in low yields in conventional methods can be more effectively produced.

6 Claims, 4 Drawing Sheets

(56) References Cited

OTHER PUBLICATIONS

Zwaig, N., et al., "Glycerol Kinase, the Pacemaker for the Dissimilation of Glycerol in *Escherichia coli*", "J. Bacteriol.", Jun. 1970, pp. 753-759, vol. 102, No. 3.

Kim, P., et al., "Effect of overexpression of *Actinobacillus succinogenes* phosphoenolpyruvate carboxykinase on succinate production in *Escherichia coli*", "Applied and Environmental Microbiology", Feb. 2004, pp. 1238-1241, vol. 70, No. 2.

Laivenieks, M., et al., "Cloning, sequencing, and overexpression of the *Anaerobiospirillum succiniciproducens* phosphoenolpyruvate carboxykinase (pckA) gene", "Applied and Environmental Microbiology", Jun. 1997, pp. 2273-2280, vol. 63, No. 6.

Qian, Z., et al., "Metabolic Engineering of *Escherichia coli* for the Production of Putrescine: A Four Carbon Diamine", "Biotechnol. Bioeng.", Aug. 27, 2009, pp. 651-662, vol. 104, No. 4.

Samuelov, N., et al., "Whey Fermentation by *Anaerobiospirillum succiniciproducens* for Production of a Succinate-Based Animal Feed Additive", "Applied and Environmental Microbiology", May 1999, pp. 2260-2263, vol. 65, No. 5.

Van Der Werf, M., et al., "Environmental and physiological factors affecting the succinate product ratio during carbohydrate fermentation by *Actinobacillus* sp. 130Z", "Arch. Microbiol.", Jun. 1997, pp. 332-342 (Abstract), vol. 167, No. 6.

\* cited by examiner

MUTANT MICROORGANISM PRODUCING SUCCINIC ACID SIMULTANEOUSLY USING SUCROSE AND GLYCEROL, AND METHOD FOR PREPARING SUCCINIC ACID USING SAME

CROSS-REFERENCE TO RELATED APPLICATIONS

This application is a U.S. national phase under the provisions of 35 U.S.C. §371 of International Patent Application No. PCT/KR11/06382 filed Aug. 30, 2011, which in turn claims priority of Korean Patent Application No. 10-2010-0084327 filed Aug. 30, 2010. The disclosures of such international patent application and Korean priority patent application are hereby incorporated herein by reference in their respective entireties, for all purposes.

TECHNICAL FIELD

The present invention relates to a succinic acid-producing mutant microorganism that is able to utilize sucrose and glycerol simultaneously as carbon sources. More particularly, the present invention relates to a succinic acid-producing mutant microorganism that is able to utilize sucrose and glycerol simultaneously for succinic acid production, the mutant organism being obtained by relieving the mechanism of sucrose-mediated catabolite repression of glycerol in a succinic acid-producing microorganism.

BACKGROUND ART

Succinic acid is a dicarboxylic acid comprised of four carbon atoms and can be used in various industrial applications. Succinic acid can be used as a precursor of industrially important chemicals, including adipic acid, 1,4-butanediol, ethylenediamine disuccinate, itaconic acid, γ-butyrolactone, γ-aminobutyric acid, and tetrahydrofuran, and the global market size of succinic acid, including precursors thereof, is estimated to be about 15 billion dollars (McKinlay et al., Appl. Microbiol. Biotechnol., 76:727, 2007). With recent interest in environmentally sustainable development and due to decreasing oil reserves and the resulting price fluctuations, global studies on the production of bio-based succinic acid have been conducted over past decades (McKinlay et al., Appl. Microbiol. Biotechnol. 76:727, 2007; Song et al., Enzyme Microbial Technol., 39:352, 2006; Jantama et al., Biotechnol. Bioeng., 99:1140, 2008). However, any kind of strain developed to date did not make it possible to maximize the productivity and yield of succinic acid while minimizing byproduct production. When the productivity was high, the efficiency was low, and conversely, when the efficiency was high, the productivity was low. Further, when the productivity was high, large amounts of byproducts were also produced. Thus, an ideal strain that can increase productivity and yield while producing only succinic acid has not yet been developed (Jantama et al., Biotechnol. Bioeng., 99:1140, 2008).

Sucrose has a price of about ¼ of the price of glucose that is generally used to produce succinic acid by microbial fermentation. Also, with a rapid increase in global biodiesel production, glycerol is being produced as a byproduct, and thus the price thereof is decreasing due to excessive supply and an appropriate method for treating glycerol is required. Accordingly, the price of glycerol is very low and continues to decrease (Miller-Klein Associates, October 2006).

Meanwhile, most microorganisms preferentially utilize preferred carbon sources from mixtures of different carbon sources. To make it possible, most microorganisms have a catabolite repression mechanism that inhibits the utilization of non-preferred carbon sources when preferred carbon sources are available (Gorke et al., Nature Reviews, 6:613, 2008). With respect to the preferential utilization of carbon sources regulated by a catabolite repression mechanism, it is well known that *E. coli* shows diauxic growth in the presence of both glucose and lactose, as reported by Monod et al. in 1942. Herein, the preferred carbon source is glucose, and thus *E. coli* shows a diauxic growth curve in which the non-preferred carbon source lactose starts to be consumed after a short lag phase after glucose has been completely consumed. Also, because of this catabolite repression mechanism, it is very difficult for general *Mannheimia* strains to utilize sucrose and glycerol at the same time. Nevertheless, the utilization of glycerol as a carbon source offers many advantages. Glycerol is highly reduced and when it is used as a carbon source, reducing equivalents (NADH, NADPH, $FADH_2$, etc.) are produced in an amount two times larger than sugars such as glucose, xylose and sucrose during the production of the intermediate phosphoenolpyruvate (PEP). Thus, glycerol is an attractive carbon source for the production of reducing chemicals (Yazdani et al., Curr. Opin. Biotechnol., 18:213, 2007). However, in many cases, the rate of growth of cells by the utilization of glycerol under anaerobic conditions is slower than that by the utilization of other sugars, and thus the utilization of glycerol as a single carbon source is advantageous in terms of reducing power, but has a limitation in increasing the productivity of a desired biological product because it shows slow growth rate.

To overcome this limitation, if the utilization rate of glycerol can be increased while utilizing sugars such as sucrose, which have a higher utilization rate than glycerol and enable cell growth at a higher level and rate, cells can be growth at a high rate while using the advantage of the high reducing power of glycerol, and thus reducing compounds, particularly succinic acid, can be effectively produced.

Accordingly, the present inventors have made extensive efforts to develop a method of producing high-purity succinic acid with high efficiency by using inexpensive sucrose and glycerol simultaneously, and as a result, have found that, when a succinic acid-producing mutant microorganism, obtained by deleting a fructose phosphotransferase-encoding gene from a succinic acid-producing microorganism or introducing a glycerol kinase-encoding gene into the microorganism, is cultured, the catabolite repression mechanism in the mutant microorganism is relieved so that the mutant microorganism can produce succinic acid using sucrose and glycerol simultaneously, minimize the production of byproducts, and produce homo-succinic acid with high efficiency and a very high productivity which could not be attained in conventional methods, thereby completing the present invention.

DISCLOSURE OF INVENTION

Technical Problem

It is an object of the present invention to a mutant microorganism wherein the catabolite repression mechanism was relieved so that the microorganism is able to utilize sucrose and glycerol simultaneously to maximize the production yield of succinic acid so as to approach the theoretical level while minimizing the production of byproducts to thereby produce homo-succinic acid.

Another object of the present invention is to provide a method of producing homo-succinic acid in said mutant microorganism using sucrose and glycerol as carbon sources under anaerobic conditions without producing byproducts.

Technical Solution

To achieve the above objects, the present invention provides a mutant microorganism that is able to utilize sucrose and glycerol simultaneously for succinic acid production, the mutant microorganism being obtained by relieving the mechanism of sucrose-mediated catabolite repression of glycerol in a succinic acid-producing microorganism.

The present invention also provides a method for preparing a mutant microorganism that is able to utilize sucrose and glycerol for succinic acid production, the method comprising relieving the mechanism of sucrose-mediated catabolite repression of glycerol in a succinic acid-producing microorganism.

The present invention also provides a method for producing succinic acid, the method comprising the steps of: culturing the above succinic acid-producing mutant microorganism under anaerobic conditions; and recovering succinic acid from the culture broth.

BRIEF DESCRIPTION OF THE DRAWINGS

FIG. 1A shows the general metabolic pathways of sucrose and glycerol and the catabolite repression mechanism therebetween, and FIG. 1B shows portions of FIG. 1A, which may be metabolically engineered in order to relieve the catabolite repression mechanism (GLY, glycerol; G3P, glycerol 3-phosphate; SCR, sucrose; G6P, glucose 6-phosphate; FRU, fructose; F1P, fructose 1-phosphate; FBP, fructose 1,6-bisphosphate; PEP, phosphoenolpyruvate; SUC, succinic acid; PYR, pyruvic acid; IIBCF, fructose PTS IIBC unit; IIBCS, sucrose PTS IIBC unit; EI, enzyme I; HPr, histidine protein; IIA, PTS enzyme IIA; Fpr, bifunctional fructose-specific IIA/HPr protein; AC, adenylate cyclase; cAMP, cyclic AMP; CRP, cAMP receptor protein).

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein are well known and are commonly employed in the art.

In one aspect, the present invention is directed to a mutant microorganism that is able to utilize sucrose and glycerol simultaneously for succinic acid production, the mutant microorganism being obtained by relieving the mechanism of sucrose-mediated catabolite repression of glycerol in a succinic acid-producing microorganism.

As used herein, the term "catabolite repression mechanism" refers to a mechanism that represses the microbial utilization of a non-preferred carbon source in the presence of a preferred carbon source when the microorganism is cultured in a medium where various carbon sources are present (Gorke et al., Nature Reviews, 6:613, 2008).

In a *Mannheimia* strain which is a succinic acid-producing strain, sucrose and glycerol could not be used simultaneously for the production of succinic acid due to the catabolite repression mechanism.

Generally, when sucrose and glycerol are present simultaneously, glycerol is consumed after sucrose that is a preferred carbon source has been consumed. Also, *Mannheimia* prefers sucrose to glucose so that it more rapidly metabolizes sucrose when sucrose and glycerol are present simultaneously.

The present invention aims to artificially relieve this catabolite repression mechanism.

The catabolite repression mechanism can be largely divided into two: transcriptional repression, and allosteric repression (Deutscher et al., Microbiol. Mol. Biol. Rev., 70:939, 2006; Gorke et al., Nature reviews, 6:613, 2008; Pettigrew et al., J. Bacteriol., 178:2846, 1996; Zwaig et al., J. Bacteriol., 102:753, 1970). With respect to transcriptional repression, the GlpR regulator represses the transcription of genes that are involved in the intracellular transport and utilization of glycerol. As used herein, the term "allosteric repression" refers to the decrease in glycerol kinase activity caused by the binding of fructose 1,6-bisphosphate (FBP) or EIIA to glycerol kinase that plays a key role in glycerol metabolism. In an environment in which sucrose and glycerol are present simultaneously, the transcriptional repression by the GlpR regulator and the allosteric repression by FBP and EIIA occur simultaneously so that glycerol metabolism is generally repressed. A strategy capable of relieving this catabolite repression mechanism avoids the transcriptional repression caused by GlpR and the allosteric repression caused by FBP and EIIA.

Figure 1:
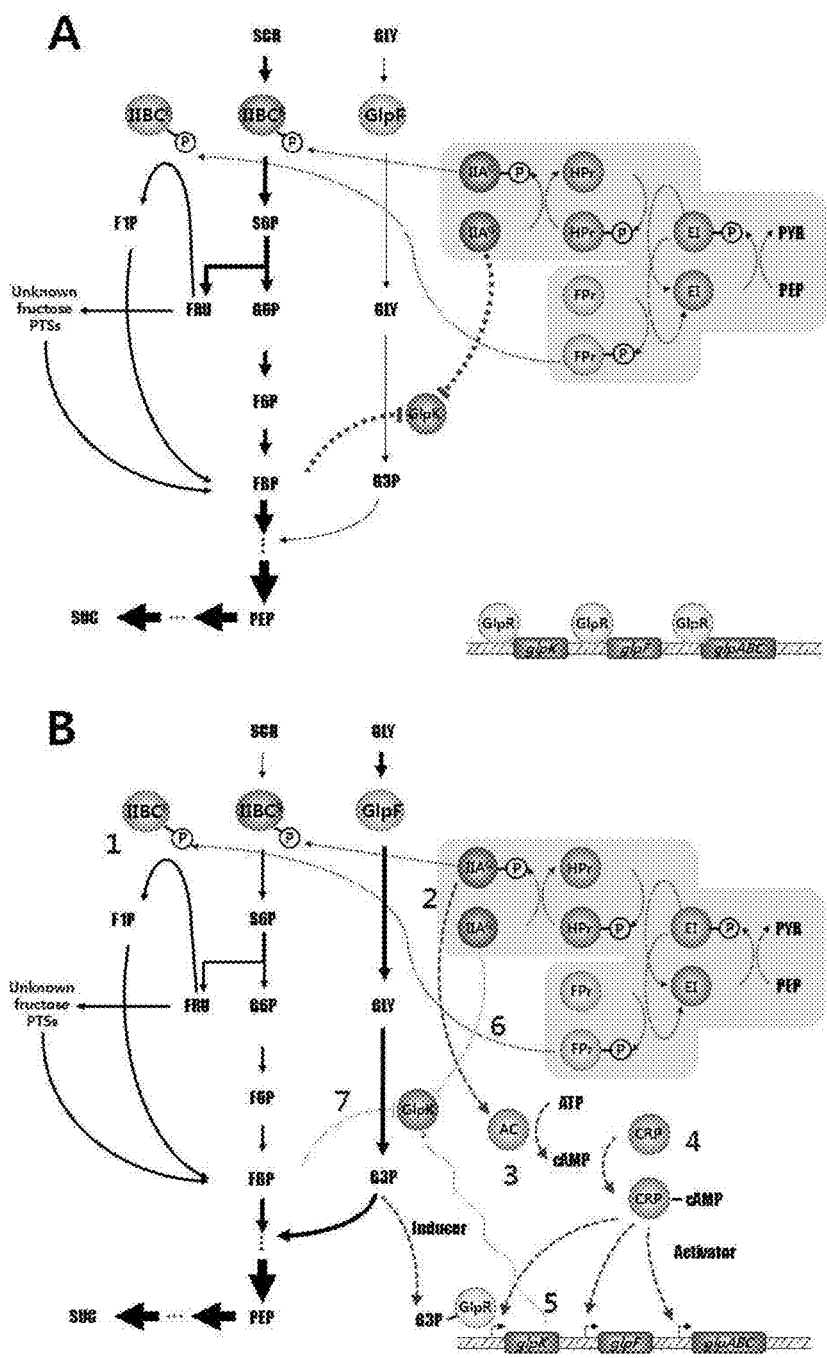
FIG. 1 schematically shows the metabolic pathways of sucrose and glycerol and the catabolite repression mechanism in a *Mannheimia* strain. Specifically.

FIG. 1 schematically shows the metabolic pathways of sucrose and glycerol and the catabolite repression mechanism in a *Mannheimia* strain. Specifically, FIG. 1A shows the general metabolic pathways of sucrose and glycerol and the catabolite repression mechanism therebetween, and FIG. 1B shows portions of FIG. 1A, which may be metabolically engineered in order to relieve the catabolite repression mechanism. In FIG. 1, the solid line arrows indicate the metabolic pathways of sucrose and glycerol, and the thickness thereof indicates the relative metabolic rate. The thin dotted arrows indicate a process in which a phosphoryl group is transferred continuously from PEP to a PTS IIBC unit, and the thick dotted arrows schematically show various pathways capable of inducing the expression of the glp operon, including a pathway starting from phosphorylated IIA, a pathway starting from adenylate cyclase (AC), a pathway starting form CRP-cAMP, a pathway starting from G3P-GlpR, etc. The thick dotted lines having a T shape at the end indicate the relative degree of allosteric repression caused by non-phosphorylated IIA and/or fructose 1,6-bisphosphate (FBP) applied to glycerol kinase (GlpK) that plays a key role in the glp operon.

As shown in FIG. 1A, the mechanism of sucrose-mediated catabolite repression of glycerol is largely divided into transcriptional repression by GlpR or the like, and allosteric repression by FBP and EIIA. As shown in FIG. 1B, methods for overcoming this repression include a method of overcoming transcriptional repression by inducing the production of various activators, a method of relieving GlpK-mediated allosteric repression by reducing the FBP or IIA concentration, and the like.

For example, there is a method in which IIBCF is removed from portion 1 of FIG. 1B so that the concentration of phosphorylated IIA is relatively increased to induce the expression of AC, and thus cAMP is much more produced to increase the production of CRP-cAMP, thereby inducing the expression of the glp operon. G3P produced by GlpK thus expressed additionally detaches the transcriptional repressor GlpR from the DNA binding sites of the glp regulon (glpABC, glpF, glpK, etc.) to facilitate the transcription of the genes of the glp regulon. At this time, the concentration of non-phosphorylated IIA is maintained at a relatively low level, and the overall metabolism of sucrose is reduced due to the removal of IIBCF so that the FBP concentration is relatively decreased, thereby alleviating allosteric repression. The simultaneous effects of such two factors result in an increase in glycerol metabolism.

As another example, there is a method in which the concentration of phosphorylated IIA in portion 2 of FIG. 1B is increased to induce the expression of AC, and thus cAMP is much more produced to increase the production of CRP-cAMP, thereby inducing the expression of the glp operon. G3P produced by GlpK thus expressed additionally detaches the transcriptional repressor GlpR from the DNA binding sites of the glp regulon to facilitate the transcription of the genes of the glp regulon, resulting in an increase in glycerol metabolism.

As still another example, there is a method in which the overexpression of AC in portion 3 of FIG. 1B is induced so that cAMP is much more produced to increase the production of CRP-cAMP, thereby inducing the expression of the glp operon. G3P produced by GlpK thus expressed additionally detaches the transcriptional repressor GlpR from the DNA binding sites of the glp regulon to facilitate the transcription of the genes of the glp regulon, resulting in an increase in glycerol metabolism.

As still another example, there is a method in which the overexpression of CRP in portion 4 of FIG. 1B and the overexpression of AC in portion 3 of FIG. 1B are simultaneously induced so that the production of CRP-cAMP is increased, thereby inducing the expression of the glp operon. G3P produced by GlpK thus expressed additionally detaches the transcriptional repressor GlpR from the DNA binding sites of the glp regulon to facilitate the transcription of the genes of the glp regulon, resulting in an increase in glycerol metabolism.

As still another example, there is a method in which the overexpression of CRP in portion 4 of FIG. 1B is induced so that the production of CRP-cAMP is increased, thereby inducing the expression of the glp operon. G3P produced by GlpK thus expressed additionally detaches the transcriptional repressor GlpR from the DNA binding sites of the glp regulon to facilitate the transcription of the genes of the glp regulon, resulting in an increase in glycerol metabolism.

As still another example, there is a method in which the overexpression of GlpK in portion 5 of FIG. 1B is induced so that the production of G3P is increased. This detaches the transcriptional repressor GlpR from the DNA binding sites of the glp regulon to facilitate the transcription of the genes of the glp regulon, resulting in an increase in glycerol metabolism.

As still another example, there is a method in which all the genes in the glp regulon are overexpressed or various combinations of some of the genes overexpressed, resulting in an increase in glycerol metabolism.

As still another method, there is a method wherein an overexpression promoter having no site to which GlpR can bind is introduced into a promoter site for expression of each transcriptional unit of the glp regulon on the chromosome in portion 5 of FIG. 1B, so that repression by GlpR is fundamentally blocked and the glp regulon is overexpressed, resulting in an increase in glycerol metabolism.

In addition, there is a method in which GlpR is removed so that the repression of expression of the glp regulon is relieved, resulting in an increase in glycerol metabolism. As yet another example, there is a method in which the concentration of IIA and/or FBP in portions 6 and 7 of FIG. 1B is reduced so that the degree of allosteric repression by GlpK is reduced, resulting in an increase in glycerol metabolism.

In addition to the above listed methods, there are possible combinations of the above-described methods, and methods apparent therefrom, for example, a method in which glycerol kinase derived from a heterologous strain designed to undergo less allosteric repression or undergoing allosteric repression is overexpressed, resulting in an increase in glycerol metabolism. In addition, there is a method in which the catabolite repression mechanism is relieved so that glycerol metabolism can be activated.

Meanwhile, succinic acid is a typical example of this reducing chemical and is a $C_4$ compound containing two carboxylic acid groups and having PEP (phosphoenolpyruvate) as an intermediate precursor. Also, succinic acid-producing microorganisms refer to microorganisms that produce larger amounts of succinic acid than other metabolites and can be commercially used to produce succinic acid by fermentation. Typical succinic acid-producing microorganisms include rumen bacteria. Known rumen bacteria include *Actinobacillus* sp., *Anaerobiospirillum* sp., and *Mannheimia* sp. (including *Basfia* sp. *Basfia* sp. was named "*Mannheimia*" when originally isolated, which was named "*Basfia* sp." later, and the 16S rRNA sequence is 99.8% identical to that of *Mannheimia* sp. Thus, *Basfia* sp. is also named "*Mannheimia* sp." in the present invention/Scholten et al., WO2009/024294A1; Kuhnert et al., Int. J. Syst. Evol. Microbiol., 60:44). From partial genetic information (16s rRNA), enzyme analysis, and fermentation results of various rumen bacteria known to produce succinic acid until now, it was found that a main biosynthesis pathway for succinic acid production from a carbon source in these rumen bacteria is almost identical with a biosynthesis pathway for succinic acid production in *Mannheimia* sp. which is a kind of rumen bacteria. Especially all rumen bacteria which are involved in the production of succinic acid convert $C_3$ compounds (phosphoenolpyruvate and pyruvate) into $C_4$ compound (oxaloacetate and malate) using $CO_2$-fixing enzyme and converts the $C_4$ compounds into fumarate, thus producing succinic acid (Zeikus et al., Appl. Microbiol. Biotechnol., 51:545, 1999; Lee et al., Appl. Environ. Microbiol., 72:1939, 2006). In other words, all rumen bacteria, including *Mannheimia* sp., have the same pathway for succinic acid biosynthesis, and this it will be apparent to those skilled in the art that the genetic mutation of the present invention can be applied to rumen bacteria-derived succinic acid-producing strains in addition to *M. succiniciproducens* shown in the examples of the present invention.

In the present invention, the succinic acid-producing microorganism may be a rumen bacterium. The rumen bacterium may be selected from the group consisting of *Mannheimia* sp., *Actinobacillus* sp., and *Anaerobiospirillum* sp.

In the present invention, the *Mannheimia* sp. strain may be *Mannheimia succiniciproducens* PALK (KCTC10973BP).

In the present invention, relieving the catabolite repression mechanism may be performed by deleting a gene encoding fructose phosphotransferase, and the mutant microorganism may be *Mannheimia succiniciproducens* PALFK (KCTC11694BP).

In the present invention relieving the catabolite repression mechanism may be performed by introducing a gene encoding glycerol kinase, and the succinic acid-producing mutant microorganism may be *Mannheimia succiniciproducens* PALFK (KCTC11694BP).

In the present invention, a succinic acid-producing mutant microorganism which produces a maximum yield of succinic acid without producing other organic acid was constructed by genetically engineering a rumen bacterium which is a succinic acid-producing microorganism.

In one Example of the present invention, *M. succiniciproducens* PALFK (KCTC11694BP) having the ability to metabolize sucrose and glycerol simultaneously was constructed by deleting a fructose phosphotransferase-encoding gene (fruA) from the genomic DNA of *Mannheimia succiniciproducens* PALK (KCTC10973BP). The constructed strain produces succinic acid with high yield and productivity without producing byproducts.

In the present invention, deletion of each of the genes was performed by inactivating the gene of interest using a homologous recombination method. However, any gene engineering method may be used without particular limitation in the present invention, as long as it can modify or eliminate the gene of interest so that an enzyme encoded by the gene of interest is not produced.

In the present invention, the culture of the succinic acid-producing mutant microorganism and the recovery of succinic acid can be performed using any methods known in conventional fermentation processes.

In the present invention, the yield of succinic acid, the production of byproducts and the ability to metabolize carbon sources were compared between *M. succiniciproducens* PALFK (KCTC11694BP) and a conventional mutant strain (*M. succiniciproducens* PALK (KCTC10973BP)). *M. succiniciproducens* PALK (KCTC10973BP) is a mutant microorganism obtained by deleting a lactate dehydrogenase-encoding gene (ldhA), a phosphotransacetylase-encoding gene (pta) and an acetate kinase-encoding gene (ackA) from the genome of a *Mannheimia* sp. strain and is the parent strain of the invention mutant microorganism *M. succiniciproducens* PALFK (KCTC11694BP) wherein a fructose phosphotransferase-encoding gene (fruA) is not deleted.

In the succinic acid-producing mutant microorganism *M. succiniciproducens* PALFK (KCTC11694BP) according to the present invention, the production of byproducts, including lactic acid, pyruvic acid, acetic acid and formic acid, was minimized and the production yield of succinic acid was increased to approach the theoretical yield (1.71-1.86 mol/mol), compared to those in the succinic acid-producing mutant strain *M. succiniciproducens* PALFK (KCTC10973BP), suggesting that it is an excellent strain for producing succinic acid.

In another aspect, the present invention is directed to a method for preparing a mutant microorganism that is able to utilize sucrose and glycerol for succinic acid production, the method comprising relieving the mechanism of sucrose-mediated catabolite repression of glycerol in a succinic acid-producing microorganism.

In another Example of the present invention, *M. succiniciproducens* PALKG (KCTC11693BP) having the ability to metabolize sucrose and glycerol simultaneously was constructed by introducing an *E. coli* glycerol kinase-encoding gene into the genomic DNA of *Mannheimia succiniciproducens* PALK (KCTC10973BP). The constructed strain produces succinic acid with high productivity and yield without producing byproducts.

The succinic acid-producing microorganism *M. succiniciproducens* PALKG (KCTC11693BP) was also compared in the above-described manner.

In still another aspect, the present invention also provides a method for producing succinic acid, the method comprising the steps of: culturing the above succinic acid-producing mutant microorganism under anaerobic conditions; and recovering succinic acid from the culture broth.

In the present invention, the culture may be performed in a medium containing both sucrose and glycerol, and the amount of other organic acids produced as byproducts may be 1 wt % or less based on the amount of succinic acid produced.

In yet another aspect, the present invention is also directed to a method for producing succinic acid with increased productivity, the method comprising the steps of: (a) culturing under anaerobic conditions either a mutant microorganism that produces succinic acid with high yield while producing little or no byproducts or a mutant microorganism obtained by relieving the mechanism of sucrose-mediated catabolite repression of glycerol so as to be able to utilize sucrose and glycerol simultaneously; (b) concentrating cells of the microorganism in the culture broth to high concentration; (c) culturing the high-concentration cells; and (d) recovering succinic acid from the culture broth.

In the present invention, step (b) of concentrating the cells in the culture broth to high concentration may be performed by an inoculum method of inoculating a high concentration of the producing strain or a membrane cell recycling bioreactor (MCRB) method (hereinafter referred to as "MCRB method").

According to the method for producing succinic acid using the inventive mutant microorganism which can utilize sucrose and glycerol simultaneously for succinic acid production, succinic acid can be produced without byproducts with an ultra-high yield approaching the theoretical yield. Also, sucrose has a price of about ¼ of the price of glucose that is generally used to produce succinic acid by microbial fermentation. Also, with a rapid increase in global biodiesel production, glycerol is being produced as a byproduct, and thus the price thereof is decreasing due to excessive supply and an appropriate method for treating glycerol is required. Accordingly, the price of glycerol is very low and continues to decrease (Miller-Klein Associates, October 2006). The method for producing succinic acid according to the present invention is highly valuable in that it can cost-effectively produce succinic acid by microbial fermentation, not a chemical synthetic method requiring huge raw material costs, produces succinic acid with an ultra-high yield approaching the theoretical yield, and produces succinic acid with an ultra-high purity so that the costs for separation and purification can be minimized.

The use of the PALFK strain according to the present invention enables homo-succinic acid to be produced without byproducts with a very high yield approaching the theoretical yield (1.71 to 1.86 mol/mol). Three factors, including productivity, yield, and byproducts/succinic acid ratio, are the most key factors in the industrialization of a succinic acid production process. Specifically, the productivity associated with initial capital cost and energy cost, and the yield is a measure for the effective use of raw materials and is associated with the raw material cost that occupies a significant portion of the cost of a bio-process, and the byproducts/succinic acid ratio is associated with the separation and purification cost that occupies half or more of the overall cost of a bio-process.

Thus, in one example of the present invention, using the PALFK strain, the yield was maximized and the byproducts/succinic acid ratio was minimized, whereby two of the above-mentioned three key factors (yield and byproducts/succinic acid ratio) were improved to the highest attainable levels. In addition, extensive efforts were made to find a method for improving the productivity, and as a result, it was found that the inoculum method and the MCRB method increase the concentration of cells in a culture and improve the succinic acid productivity by at least 2 times and 10 times, respectively, that of the parent strain.

EXAMPLES

Hereinafter, the present invention will be described in further detail with reference to examples. It will be obvious to a person having ordinary skill in the art that these examples are illustrative purposes only and are not to be construed to limit the scope of the present invention.

Particularly, the following examples illustrate only a specific vector and *Mannheimia* sp. which is a succinic acid-producing microorganism as a host cell in order to delete the genes according to the present invention. However, it will be obvious to a person skilled in the art that the use of other kinds of succinic acid-producing microorganisms can also provide mutant microorganisms that produce high-purity succinic acid.

Example 1

Construction of fruA-Deleted Vector (pSacHRO6fruA)

In order to delete the fruA gene (fructose phosphotransferase-encoding gene) from the genome of a succinic acid-producing microorganism by homologous recombination, a gene exchange vector was constructed in the following manner. First, PCR was performed using the genomic DNA of *M. succiniciproducens* MBEL55E (KCTC0769BP) as a template and each of a primer pair of SEQ ID NOS: 1 and 2, a primer pair of SEQ ID NOS: 3 and 4 and a primer pair of SEQ ID NOS: 5 and 6, thereby obtaining PCR fragments containing a fruA left homologous region (HL), a chloramphenicol (Cm) resistance gene and a fruA right homologous region (HR), respectively.

Then, overlapping PCR was performed using the above three PCR fragments as a template and primers of SEQ ID NOS: 1 and 6, and the resulting DNA fragment was digested with SacI and PstI and introduced into a pSacHR06 vector, thereby constructing a pSacHR06fruA vector.

SEQ ID NO: 1:
5'-ATCGCGGATCCGGTGGAAACCCTCGGTTTATT

SEQ ID NO: 2:
5'-AATCTGCTCTGATGCGCAGCTAAAACCTGGTGCAATA

SEQ ID NO: 3:
5'-CCAGGTTTTAGCTGCGCATCAGAGCAGATTGTACTGAGAG

-continued

SEQ ID NO: 4:
5'-AATTACACTTGAAACCCTGATTCTGTGGATAACCGTATTAC

SEQ ID NO: 5:
5'-ATCCACAGAATCAGGGTTTCAAGTGTAATTGGCGGAG

SEQ ID NO: 6:
5'-TCGACGCGTCGACTTCATCTAACCCCAACGCTTG

Example 2

Construction of *M. succiniciproducens* PALFK Strain

A mutant strain was constructed by deleting fruA from the genome of *M. succiniciproducens* PALK (KCTC10973BP) using the vector pSacHR06fruA for deleting the fruA gene, constructed in Example 1.

Specifically, *M. succiniciproducens* PALK (KCTC10973BP) was plated on BHI (Brain-Heart Infusion) solid medium and cultured at 39° C. for 36 hours. The colony formed was inoculated in 10 mL of BHI liquid medium and cultured for 12 hours. The sufficiently grown cell culture broth was inoculated in 100 mL of BHI liquid medium at a concentration of 1% and cultured in a stationary incubator for 39° C.

When the culture broth reached an $OD_{600}$ of about 0.3-0.5 after about 4-5 hours, it was maintained at 0-4° C. for 20 minutes such that the cells were no longer grown. Then, the culture broth was centrifuged at 4° C. at 4,500 rpm for 15 minutes to collect cells. Then, the cells were resuspended in 200 mL of 10% glycerol solution at 4° C. and centrifuged under the above-described conditions. This resuspension and centrifugation were performed a total of three times while reducing the volume of 10% glycerol solution by ½ for each time. The resulting cells were resuspended in the same volume of 10% glycerol solution, dispensed and stored at −80° C.

The cell concentrate suspension obtained as described above was mixed with the gene deletion vector pSacHR06fruA constructed in Example 1 and was electroporated under the conditions of 2.5 kV, 25 μF and 200 ohms to transform *M. succiniciproducens* PALK (KCTC10973BP) with the vector. The electroporated cells were added to BHI liquid medium and incubated in a stationary incubator at 39° C. for 1 hour. Then, the culture broth was plated on BHI solid medium containing 6.8 μg/mL of antibiotic chloramphenicol and incubated in a stationary incubator at 39° C. for 48 hours or more. In order to select a colony where double crossover has occurred, the colonies formed were plated on BHI solid medium containing chloramphenicol (6.8 μg/mL) and 100 g/L of sucrose and cultured for 24 hours, after which the colonies formed were plated again on the same medium.

The mutant strain formed on the medium was cultured in antibiotic-containing BHI liquid medium, and genomic DNA was isolated from the cultured strain by the method of Rochelle et al (Rochelle et al., *FEMS Microbiol. Lett.*, 100:59, 1992). PCR was performed using the isolated genomic DNA of the mutant strain as a temperature, and the PCR product was electrophoresed to confirm whether the fruA gene has been deleted from the genomic DNA. Whether the fruA gene has been deleted was confirmed by performing PCR twice in the following manner. First, PCR was performed using the genomic DNA of the mutant strain as a template and each of a primer pair of SEQ ID NOS: 7 and 8 and a primer pair of SEQ ID NOS: 9 and 10. The PCR fragments of the two PCRs were electrophoresed to confirm the deletion of the fruA by their size. As a result, *M. succiniciproducens* PALFK (KCTC11694BP) was constructed and deposited under accession number KCTC11694BP in the Korean Collection for Type Cultures, Korean Research Institute of Bioscience and Biotechnology.

```
SEQ ID NO: 7:
5'-CTATGATTTGGTCGGGCGTTT

SEQ ID NO: 8:
5'-TGAATGGCAGAAATTCGAAA

SEQ ID NO: 9:
5'-TGATCTTCCGTCACAGGTAT

SEQ ID NO: 10:
5''TTGACCGCACTTTGCACATC
```

Example 3

Construction of pME18glpK22 Vector And Construction of *M. succiniciproducens* PALKG Strain Introduced With the Vector In order to obtain a DNA containing an *E. coli* glycerol kinase-encoding gene (glpK22), PCR was performed using the genomic DNA of *Escherichia coli* K-12 MG1655 (ATCC 47076; American Type Culture Collection, Manassas, Va., USA) and each of a primer pair of SEQ ID NOS: 11 and 12, a primer pair of SEQ ID NOS: 13 and 14 and a primer pair of SEQ ID NOS: 15 and 16. Then, PCR was performed using the resulting three PCR products as a template. The PCR product contained the glpK22 gene in which the 913$^{th}$ base pair of the coding sequence has adenosine converted from guanine of the glpK gene of the original *E. coli* K-12 MG1655. It is known that the glycerol kinase which is expressed from the glpK gene undergoes less allosteric repression caused by FBP and IIA than non-mutated glpK. (Pettigrew et al., J. Bacteriol., 178:2846, 1996).

```
SEQ ID NO: 11:
5'-ACTCCGGAATTCAACGCACTGACAATCTCACTT

SEQ ID NO: 12:
5'-CAGCGAAGCTTTTTGGGTAGAAAGTATAAAGACAGAATCACA

SEQ ID NO: 13:
5'-TTTATACTTTCTACCCAAAAAGCTTCGCTGTAATATG

SEQ ID NO: 14:
5'-CCATAAACACCGCACTTTCCAACGCATAGTTCACTTC

SEQ ID NO: 15:
5'-AACTATGCGTTGGAAAGTGCGGTGTTTATGGCAGG

SEQ ID NO: 16:
5'-ACCTGCGAGCTCATTATTGATGTGTGCGGGGT
```

The PCR product obtained as described above was cloned into the EcoRI and SacI sites of pME18 (fang et al., *Appl. Environ. Microbiol.*, 73:5411, 2007), thereby constructing a pME18glpK22 vector. Also, the vector was sequenced using primers of SEQ ID NOS: 17 to 21 by Solgent (Korea).

```
SEQ ID NO: 17:
5'-TAGCTATGTGTTAAAGCCTT

SEQ ID NO: 18:
5'-ACCAGGGCACCACCAGCTCC

SEQ ID NO: 19:
5'-CCGATTACACCAACGCCTCT

SEQ ID NO: 20:
5'-ATGTGGTTCCGGCATTTACC

SEQ ID NO: 21:
5'-TTATGCCGCATCCGGTAGTCCC
```

The pME18glpK22 vector constructed as described above was introduced into *M. succiniciproducens* PALK (KCTC10973BP) to construct a *M. succiniciproducens* PALKG (KCTC11693BP) strain. In order to introduce the expression vector, the preparation and electroporation of a cell concentrate suspension were performed as described in Example 2, and the cells were plated on BHI solid medium containing 25 µg/mL of ampicillin in place of chloramphenicol and were cultured in a. stationary incubator at. 39° C. for 48 hours. The pure colony formed was cultured in BHI liquid medium for 8 hours, and then mixed with glycerol solution to a final concentration of 15% (w/v), after which the cell solution was stored at −80° C. until use.

Example 4

Production of Homo-Succinic Acid Using *M. succiniciproducens* PALFK Strain And PALFK Strain The *M. succiniciproducens* PALFK (KCTC11694BP) or PALKG (KCTC11693BP) strain constructed in Examples 2 and 3 was cultured in 10 mL of MH5 medium (per liter, 2.5 g yeast extract, 2.5 g polypeptone, 1 g NaCl, 0.02 g $CaCl_2.2H_2O$, 0.2 g $MgCl_2.6H_2O$, 8.7 g $K_2HPO_4$, and 10.0 g $NaHCO_3$) containing 10 g/L of sucrose and was cultured under anaerobic conditions at 39° C. for 8 hours. Then, the strain was cultured in 300 mL of the same medium. For fermentation, the culture broth was inoculated in a microbial reactor (Bioflo 3000, New Brunswick Scientific Co., Edison, N.J., USA) containing 2.5L of synthetic medium (per liter, 1 g NaCl, 2 g $(NH_4)_2HPO_4$, 0.02 g $CaCl_2.2H_2O$, 0.2 g $MgCl_2.6H_2O$, 8.709 g $K_2HPO_4$, 0.5 g cysteine, 0.5 g methionine, 0.5 g alanine, 0.5 g asparagine, 0.5 g aspartic acid, 2.46 g proline, 0.5 g serine, 0.005 g nicotinic acid, 0.005g Ca-pantothenate, 0.005 g pyridoxine.HCl, 0.005 g thiamine, 0.005 g ascorbic acid and 0.005 g biotin). The fermentation was performed under the conditions of initial sucrose concentration of 22.25 g/L (65 mM), initial glycerol concentration of 4.6 g/L (50 mM), temperature of 39° C. and 200 rpm while pure carbon dioxide was fed into the reactor at a rate of 0.2 vvm (carbon dioxide volume/incubator working volume/min). During fermentation, the culture broth was adjusted to a pH of 6.5 with ammonia water, and the following antibiotics were added: 50 µg/mL of spectinomycin for PALK, 6.8 µg/mL of chloramphenicol for PALFK, and 25 µg/mL of ampicillin for PALKG. For production of high-concentration succinic acid, when the carbon sources were completely consumed, 700 g/L of sucrose and glycerol solution was semi-continuously added to the culture broth. For comparison with the performance of the PALFK, *M. succiniciproducens* PALK (KCTC10973BP) which is a succinic acid-producing strain was cultured in the same manner as described above. The concentration of cells in the culture broth was measured with a spectrophotometer and calculated using the previously measured absorbance of the spectrophotometer and a verification test for dried-cell weight. During the fermentation, samples were collected from the bioreactor regularly. The collected samples were centrifuged at 13,000 rpm for 10 minutes, and then the concentrations of various metabolites, succinic acid, sucrose and glycerol in the supernatants were analyzed by high-performance liquid chromatography (HPLC).

Figure 2:
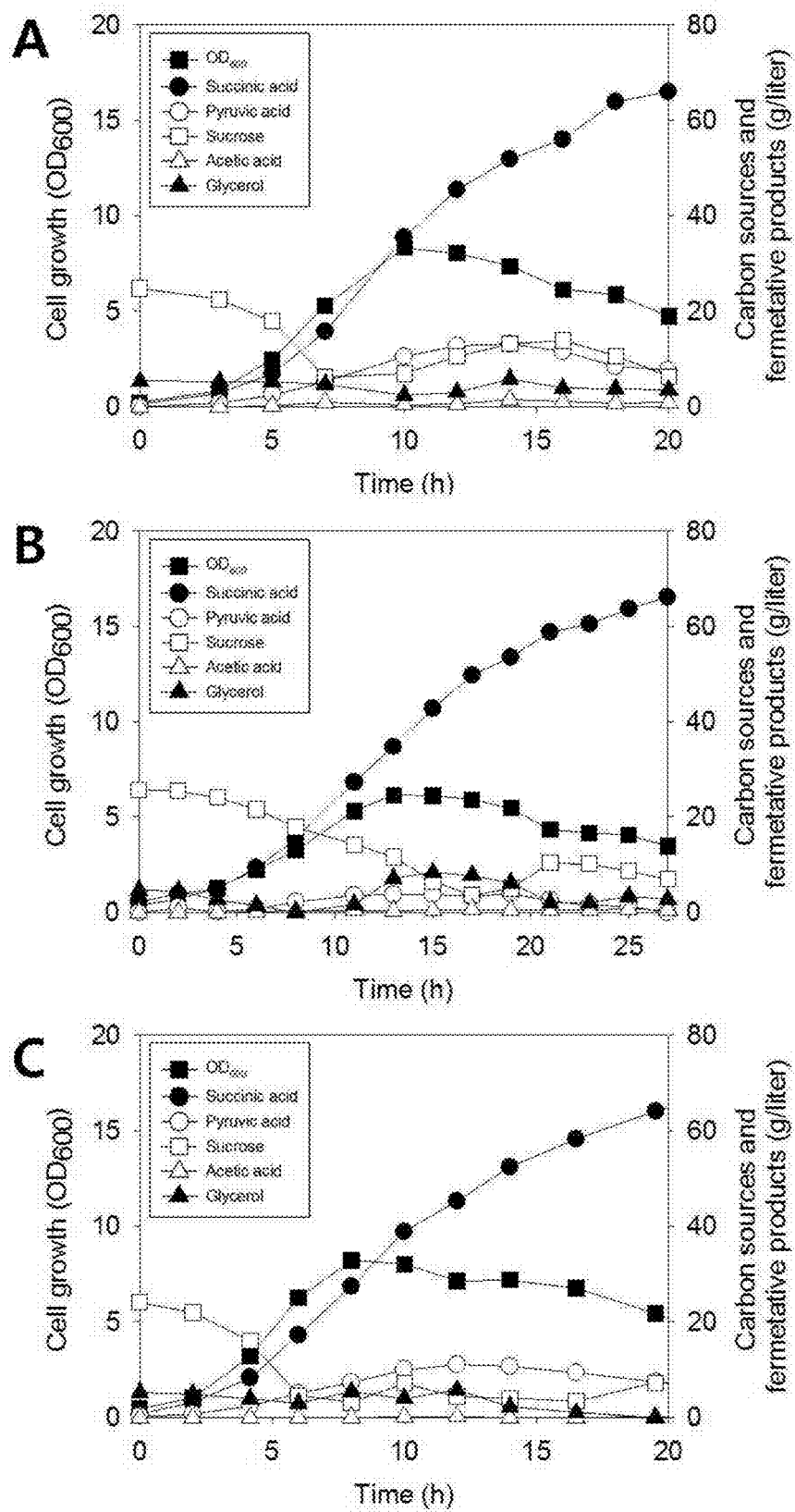
FIG. 2 is a set of graphs showing the cell growth and metabolite production obtained in the fed-batch culture of *M. succiniciproducens* PALK (FIG. 2A), *M. succiniciproducens* PALFK (FIG. 2B) and *M. succiniciproducens* PALK (FIG. 2C).

As a result, as shown in FIG. 2 and Table 1, *M. succiniciproducens* PALFK (KCTC11694BP) showed a higher succinic acid production yield than *M. succiniciproducens* PALK (KCTC10973BP) and produced high-purity succinic acid without producing byproducts. The uptake of glycerol showing the same degree of reduction as succinic acid increased by about 7 times, and this glycerol uptake is connected directly with the production of decreased amounts of byproducts, because pyruvate production which is connected directly with byproduct production is not mediated, unlike when sucrose is used. In addition, the increased uptake of glycerol enables a decreased amount of sucrose to be used, so that homo-succinic acid is produced in high yield using decreased amounts of carbon sources.

Also, *M. succiniciproducens* PALKG (KCTC11693BP) showed a pattern slightly different from the PALFK strain, in that the utilization of glycerol in the PALKG strain was increased in the range that did not impair sucrose utilization and cell growth, and thus the accumulation of pyruvate was maintained at the level equal to that in the PALK strain. Nevertheless, the ability of the PALKG strain to utilize glycerol was at least two times higher than that of the PALK strain, and as a result, the PALKG strain produced succinic acid in a yield of 1.39 mol/mol which was higher than that of the PALK strain (1.24 mol/mol).

TABLE 1

Characteristics of culture of *Mannheimia* strains

| Strain | PALK | PALFK | PALKG |
|---|---|---|---|
| Sucrose (g/L) | 77.88 | 39.80 | 61.87 |
| Glycerol (g/L) | 5.52 | 29.75 | 11.84 |
| Succinic acid (g/L) | 65.05 | 68.41 | 64.67 |
| Pyruvic acid (g/L) | 8.00 | 0 | 7.70 |
| Acetic acid (g/L) | 1.43 | 1.03 | 0.62 |
| Total byproducts (g/L) | 9.44 | 1.03 | 8.32 |
| Byproducts/succinic acid | 0.15 | 0.02 | 0.13 |
| Yield (mol/mol) | 1.24 | 1.57 | 1.39 |

*Values for sucrose and glycerol are values expressed as uptake, and values for succinic acid, pyruvic acid and acetic acid are the amounts of acids produced. Yield is a value obtained by calculating sucrose and glycerol contents based on glucose equivalent.
** Each of the values for sucrose and glycerol, the produced amount and the yield is the average of three independent experiments.

Example 5

Improvement In Succinic Acid Productivity of *M. succiniciproducens* PALFK Strain That Produces High Yield of Homo-Succinic Acid In this Example, a method for improving the succinic acid productivity of the *M. succiniciproducens* PALFK strain that produces a high yield of homo-succinic acid was examined.

As can be seen in FIG. 2B, the PALFK strain reached the highest productivity at 13-15 hours after inoculation, and the cell concentration was the highest at that time. Thus, in order to maximize succinic acid productivity, the change in productivity resulting from an increase in the cell concentration was examined.

Figure 3:
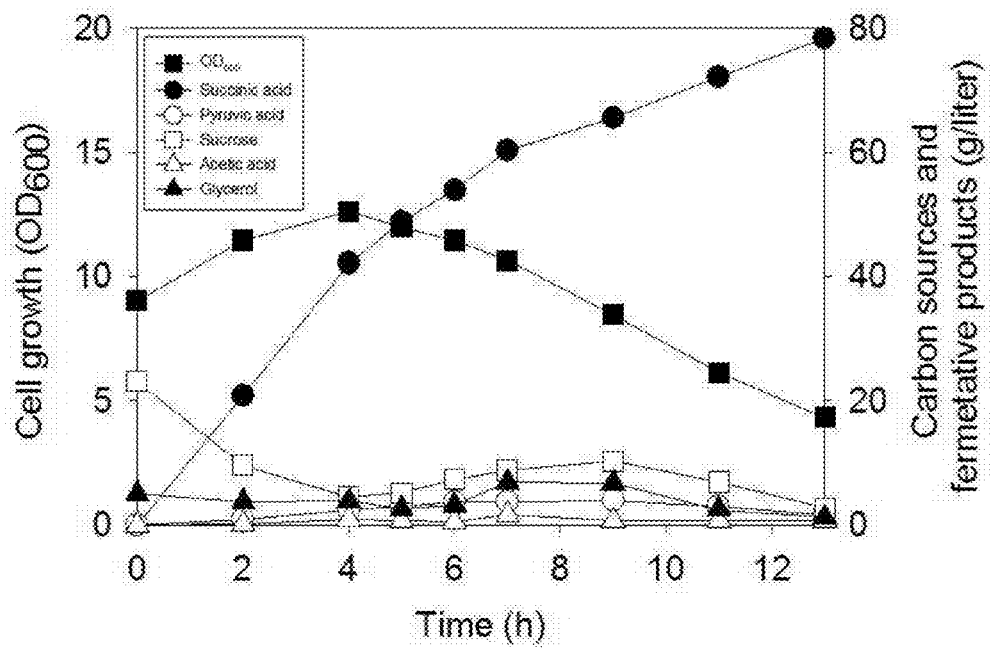
FIG. 3 is a graph showing the cell growth and metabolite production obtained in the fed-culture culture in a *M. succiniciproducens* PALFK strain inoculated in an increased amount.

In order to examine the change in succinic acid productivity, which results when the initial cell concentration of PALFK under the culture conditions as described in Example 4 are increased to $OD_{600}$=9.03, the following experiment was performed. As described in Example 4, fermentation was performed in a microbial reactor (Bioflo 3000) containing 5L of MH5 medium containing 22.25 g/L of sucrose and 10 g/L of glycerol under the conditions of temperature of 39° C. and 200 rpm while pure carbon dioxide was fed into the medium at a rate of 0.2 vvm (carbon dioxide volume/incubator working volume/minute). During fermentation, the culture broth was adjusted to a pH of 6.5 by addition of ammonia water, and 6.8 μg/mL of antibiotic crhoramphenicol was added to the medium. The cell concentration of the PALFK strain reached an $OD_{600}$ of about 4.6, the culture process was stopped, and the culture broth was centrifuged at room temperature at 6000 rpm for 10 minutes to collect cell pellets. The collected cell pellets were resuspended in 300 mL of MH5 medium to obtain a high concentration of an inoculum, which was then inoculated and cultured in synthetic medium under the conditions described in Example 4. As a result, as can be seen in FIG. 3 and Table 2, the succinic acid productivity was 6.03 g/L/h (highest productivity: 10.69 g/L/h) which was at least two times higher that than in the original conditions, and the degree of byproduct production and the yield of succinic acid were almost similar to those under the original conditions.

Figure 4:
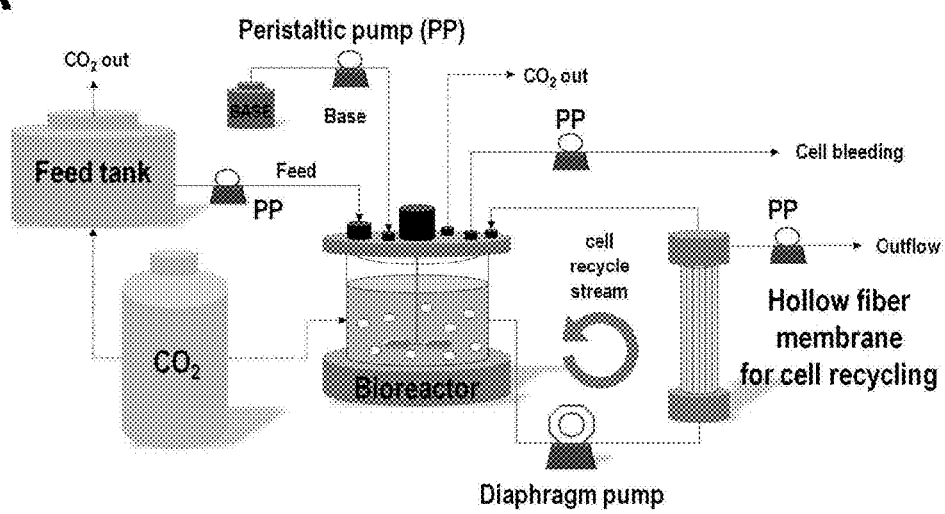
FIG. 4A is a schematic view showing a MCRB culture method, wherein the solid line indicates the flow of liquid streams (medium, cell-containing medium, metabolite-containing medium, etc.), and the dotted line indicates the flow of gas (carbon dioxide).
FIG. 4B is a graph showing the cell growth and metabolite production obtained in the culture of a *M. succiniciproducens* PALFK strain, conducted by a MCRB culture method.
Figure 4:
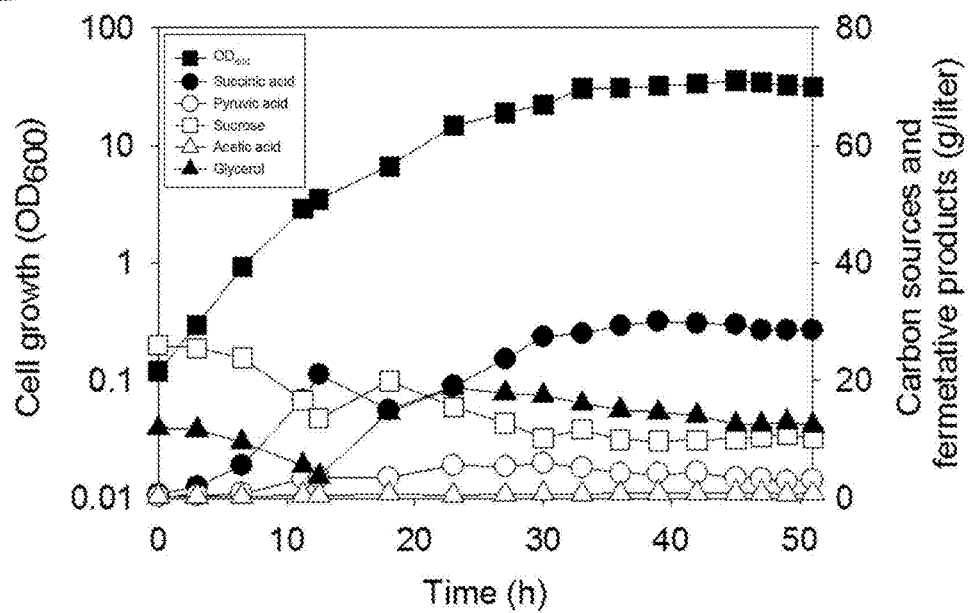

Based on these results, in order to increase artificially the cell concentration, a membrane cell recycling bioreactor (MCRB) system (FIG. 4A) was used.

In the MCRB system, a hollow fiber membrane unit (Cell-Flo Plus Module; Spectrum Laboratories Inc., Rancho Dominguez, Calif., USA) for cell recycling was connected to a Bioflo 110 reactor (New Brunswick Scientific Co.), and the working volume of the bioreactor was maintained at 0.4L. The speed of agitation in the bioreactor was maintained at 100 rpm, and a diaphragm pump for cell recycling was operated at a rate of 150 mL/min.

The composition of the synthetic medium was the same as used in Example 4, except that it contained 0.5 g/L of proline. In the bioreactor, the initial sucrose concentration was 22.25 g/L, and the initial glycerol concentration was 4.6 g/L, and in the feed tank, 30 g/L of sucrose and 21 g/L of glycerol were used. During the operation of MCRB, dilution rate (D) was maintained at 1.027 $h^{-1}$, and the cell bleeding rate that determines cell growth in a normal state was maintained at 0.015 $h^{-1}$. During the operation of MCRB, a sample was analyzed at least five times at intervals longer than the minimum turnover time (that refers to the time to reach the working volume as a function of dilution rate (D) during culture; at D=1 or 2, the time to reach the working volume is 1 h and 0.2 h) to determine the cell concentration, the production of metabolites, the consumption of carbon sources, and the like, and the state in which these measurements were maintained at constant levels was defined as the normal state.

The results of the culture performed in MCRB as described above are shown in FIG. 4B and Table 2. As can be seen therein, the succinic acid productivity of the PALFK strain was 29.73 g/L/h which was at least 10 times higher than that of the parent strain. In addition, the yield of succinic acid was maintained at the same level, and the production of byproducts was slightly higher than that in Example 4, but was maintained at a low level. In conclusion, as shown in this Example, the present inventors succeeded in producing succinic acid with an ultrahigh productivity of 29.73 g/L/h in a high efficiency (1.54 mol/mol) approaching the theoretical yield by the use of the strategy of increasing the productivity after maximizing the yield and the decrease in the production of byproducts. The succinic acid productivity shown in this Example is an ultrahigh productivity that has not yet been attained by any conventional method, and it has a great significance in that it was attained while the yield approaching the theoretical yield of 1.54 mol/mol was attained.

TABLE 2

Characteristics of culture of PALFK strain in various fermentation methods

| Fermentation type | Fed-batch | Fed-batch' | MCRB |
|---|---|---|---|
| Sucrose (g/L) | 39.80 | 53.08 | 19.71 |
| Glycerol (g/L) | 29.75 | 26.89 | 8.11 |
| Succinic acid (g/L) | 68.41 | 78.41 | 29.00 |
| Pyruvic acid (g/L) | 0 | 1.64 | 3.86 |
| Acetic acid (g/L) | 1.03 | 0.72 | 0.81 |
| Total byproducts (g/L) | 1.03 | 2.36 | 4.27 |
| Byproducts/succinic acid | 0.02 | 0.03 | 0.15 |
| Yield (mol/mol) | 1.57 | 1.64 | 1.54 |
| Maximum productivity (g/L/h) | 2.46 | 6.03 | 29.73 |
| Overall productivity (g/L/h) | 4.55 | 10.69 | 29.73 |

* Fed-batch' indicates a fed-batch inoculated with a high concentration of cells ($OD_{600}$ = 9.03 immediately after initial inoculation) during fed-batch fermentation.
** Data for fed-batch fermentation are the average of three independent experiments, and data for MCRB are the average of five samples consecutively collected after the normal state has been reached.

DEPOSIT OF MICROORGANISMS

Depository Institution: Korea Research Institute of Bioscience and Biotechnology;
Accession Number: KCTC 11693BP;
Deposit Date: May 10, 2010.
Depository Institution: Korea Research Institute of Bioscience and Biotechnology;
Accession Number: KCTC 11694BP;
Deposit Date: May 10, 2010.

INDUSTRIAL APPLICABILITY

As described above, when the succinic acid-producing mutant microorganism is cultured, it utilizes sucrose and glycerol simultaneously so that succinic acid can be produced with high productivity in a maximum yield approaching the theoretical yield while the production of byproducts is minimized. In addition, according to the present invention, various reduced chemicals which have been produced in low yields in conventional methods can be more effectively produced.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A mutant microorganism that is able to utilize sucrose and glycerol simultaneously for succinic acid production, the mutant microorganism being obtained by relieving the catabolite repression mechanism of glycerol in a succinic acid-producing microorganism, wherein the succinic acid-producing microorganism is selected from the group consisting of *Mannheimia* sp., *Actinobacillus* sp., and *Anaerobiospirillum* sp, and wherein relieving the catabolite repression mechanism is performed by deleting a gene encoding fructose phosphotransferase or by introducing a gene encoding glycerol kinase.

2. The mutant microorganism of claim 1, wherein the *Mannheimia* sp. strain is *Mannheimia succiniciproducens* PALK (KCTC10973BP).

3. The mutant microorganism of claim 2, wherein the mutant microorganism is *Mannheimia succiniciproducens* PALFK (KCTC11694BP).

4. The mutant microorganism of claim 1, wherein the succinic acid-producing mutant microorganism is *Mannheimia succiniciproducens* PALKG (KCTC11693BP).

5. A method for preparing a mutant microorganism that is able to utilize sucrose and glycerol for succinic acid production, the method comprising relieving the catabolite repression mechanism of glycerol in a succinic acid-producing microorganism, wherein the succinic acid-producing microorganism is selected from the group consisting of *Mannheimia* sp., *Actinobacillus* sp., and *Anaerobiospirillum* sp, and wherein relieving the catabolite repression mechanism is performed by deleting a gene encoding fructose phosphotransferase or by introducing a gene encoding glycerol kinase.

6. The method of claim 5, wherein the *Mannheimia* sp. strain is *Mannheimia succiniciproducens* PALK (KCTC10973BP).

* * * * *

UNITED STATES PATENT AND TRADEMARK OFFICE
CERTIFICATE OF CORRECTION

| | | |
|---|---|---|
| PATENT NO. | : 8,691,516 B2 | Page 1 of 1 |
| APPLICATION NO. | : 13/819339 | |
| DATED | : April 8, 2014 | |
| INVENTOR(S) | : Sang Yup Lee | |

It is certified that error appears in the above-identified patent and that said Letters Patent is hereby corrected as shown below:

In the Specification

Column 11, line 57:
   "(fang et al...)"
should be
   --(Jang et al...)--.

Signed and Sealed this
Twelfth Day of August, 2014

Michelle K. Lee
*Deputy Director of the United States Patent and Trademark Office*

SEQUENCE LISTING

```
<160> NUMBER OF SEQ ID NOS: 21

<210> SEQ ID NO 1
<211> LENGTH: 32
<212> TYPE: DNA
<213> ORGANISM: Artificial
<220> FEATURE:
<223> OTHER INFORMATION: primer

<400> SEQUENCE: 1
atcgcggatc cggtggaaac cctcggttta tt                                   32

<210> SEQ ID NO 2
<211> LENGTH: 37
<212> TYPE: DNA
<213> ORGANISM: Artificial
<220> FEATURE:
<223> OTHER INFORMATION: primer

<400> SEQUENCE: 2
aatctgctct gatgcgcagc taaaacctgg tgcaata                              37

<210> SEQ ID NO 3
<211> LENGTH: 40
<212> TYPE: DNA
<213> ORGANISM: Artificial
<220> FEATURE:
<223> OTHER INFORMATION: primer

<400> SEQUENCE: 3
ccaggtttta gctgcgcatc agagcagatt gtactgagag                           40

<210> SEQ ID NO 4
<211> LENGTH: 41
<212> TYPE: DNA
<213> ORGANISM: Artificial
<220> FEATURE:
```

-continued

<223> OTHER INFORMATION: primer

<400> SEQUENCE: 4
aattacactt gaaaccctga ttctgtggat aaccgtatta c          41

<210> SEQ ID NO 5
<211> LENGTH: 37
<212> TYPE: DNA
<213> ORGANISM: Artificial
<220> FEATURE:
<223> OTHER INFORMATION: primer

<400> SEQUENCE: 5
atccacagaa tcagggtttc aagtgtaatt ggcggag              37

<210> SEQ ID NO 6
<211> LENGTH: 34
<212> TYPE: DNA
<213> ORGANISM: Artificial
<220> FEATURE:
<223> OTHER INFORMATION: primer

<400> SEQUENCE: 6
tcgacgcgtc gacttcatct aaccccaacg cttg                 34

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
ctatgatttg gtcgggcgtt t                               21

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
tgaatggcag aaattcgaaa                                 20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
tgatcttccg tcacaggtat                                 20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
ttgaccgcac tttgcacatc                                 20

<210> SEQ ID NO 11

```
<211> LENGTH: 33
<212> TYPE: DNA
<213> ORGANISM: Artificial
<220> FEATURE:
<223> OTHER INFORMATION: primer

<400> SEQUENCE: 11
actccggaat tcaacgcact gacaatctca ctt                                    33

<210> SEQ ID NO 12
<211> LENGTH: 42
<212> TYPE: DNA
<213> ORGANISM: Artificial
<220> FEATURE:
<223> OTHER INFORMATION: primer

<400> SEQUENCE: 12
cagcgaagct ttttgggtag aaagtataaa gacagaatca ca                          42

<210> SEQ ID NO 13
<211> LENGTH: 37
<212> TYPE: DNA
<213> ORGANISM: Artificial
<220> FEATURE:
<223> OTHER INFORMATION: primer

<400> SEQUENCE: 13
tttatacttt ctacccaaaa agcttcgctg taatatg                                37

<210> SEQ ID NO 14
<211> LENGTH: 37
<212> TYPE: DNA
<213> ORGANISM: Artificial
<220> FEATURE:
<223> OTHER INFORMATION: primer

<400> SEQUENCE: 14
ccataaacac cgcactttcc aacgcatagt tcacttc                                37

<210> SEQ ID NO 15
<211> LENGTH: 35
<212> TYPE: DNA
<213> ORGANISM: Artificial
<220> FEATURE:
<223> OTHER INFORMATION: primer

<400> SEQUENCE: 15
aactatgcgt tggaaagtgc ggtgtttatg gcagg                                  35

<210> SEQ ID NO 16
<211> LENGTH: 32
<212> TYPE: DNA
<213> ORGANISM: Artificial
<220> FEATURE:
<223> OTHER INFORMATION: primer

<400> SEQUENCE: 16
acctgcgagc tcattattga tgtgtgcggg gt                                     32

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
```

-continued

```
tagctatgtg ttaaagcctt                                              20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
accagggcac caccagctcc                                              20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
ccgattacac caacgcctct                                              20

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
atgtggttcc ggcatttacc                                              20

<210> SEQ ID NO 21
<211> LENGTH: 22
<212> TYPE: DNA
<213> ORGANISM: Artificial
<220> FEATURE:
<223> OTHER INFORMATION: primer

<400> SEQUENCE: 21
ttatgccgca tccggtagtc cc                                           22
```